(12) United States Patent
Thompson et al.

(10) Patent No.: US 9,046,465 B2
(45) Date of Patent: Jun. 2, 2015

(54) OPTIMIZATION OF THE SOURCE FIRING PATTERN FOR X-RAY SCANNING SYSTEMS

(75) Inventors: William Thompson, Manchester (GB); William Robert Breckon Lionheart, High Peak (GB); Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 607 days.

(21) Appl. No.: 13/405,117

(22) Filed: Feb. 24, 2012

(65) Prior Publication Data

US 2012/0219116 A1 Aug. 30, 2012

Related U.S. Application Data

(60) Provisional application No. 61/446,098, filed on Feb. 24, 2011.

(51) Int. Cl.
*G01N 23/04* (2006.01)
*A61B 6/00* (2006.01)

(52) U.S. Cl.
CPC .............. *G01N 23/04* (2013.01); *A61B 6/4007* (2013.01)

(58) Field of Classification Search
CPC ................ A61B 6/4014; A61B 6/4007; H01J 2235/068; H01J 35/065; H01J 2235/062; H01J 1/3048
USPC ....................................................... 378/9, 62
See application file for complete search history.

(56) References Cited

U.S. PATENT DOCUMENTS

| | | | |
|---|---|---|---|
| 6,240,157 B1 | 5/2001 | Danielsson | |
| 6,324,243 B1 | 11/2001 | Edic et al. | |
| 2004/0066879 A1 | 4/2004 | Machida | |
| 2005/0123092 A1 | 6/2005 | Mistretta et al. | |
| 2006/0050842 A1 | 3/2006 | Wang et al. | |
| 2007/0172023 A1* | 7/2007 | Morton et al. | 378/9 |
| 2008/0056437 A1* | 3/2008 | Pack et al. | 378/10 |

OTHER PUBLICATIONS

Allenback, Analysis of sampling-pattern dependence in time sequential sampling of spatiotemporal signals, 1981, Journal of the Optical Society of America, vol. 71, No. 1, pp. 99-105.*
PCT/US10/41871 Search Report, Jan. 20, 2011, Rapiscan Systems, Inc.

* cited by examiner

*Primary Examiner* — David J Makiya
*Assistant Examiner* — John Corbett
(74) *Attorney, Agent, or Firm* — Novel IP (57) ABSTRACT

The present application discloses a computed tomography system having non-rotating X-ray sources that are programmed to optimize the source firing pattern. In one embodiment, the CT system is a fast cone-beam CT scanner which uses a fixed ring of multiple sources and fixed rings of detectors in an offset geometry. It should be appreciated that the source firing pattern is effectuated by a controller, which implements methods to determine a source firing pattern that are adapted to geometries where the X-ray sources and detector geometry are offset.

17 Claims, 9 Drawing Sheets

OPTIMIZATION OF THE SOURCE FIRING PATTERN FOR X-RAY SCANNING SYSTEMS

CROSS-REFERENCE TO RELATED APPLICATIONS

The present application claims the benefit of U.S. Provisional Patent Application No. 61/446,098, of the same title, and filed on Feb. 24, 2011, which is herein incorporated by reference in its entirety.

The present application is also related to U.S. patent application Ser. No. 13/146,645, filed on Jul. 27, 2011, which is a 371 national stage application of PCT/GB2010/050125, filed on Jan. 27, 2010 and which, in turn, relies in Great Britain Application No. 0901338.4, filed on Jan. 28, 2009, for priority. Each of the aforementioned applications is hereby incorporated by reference in its entirety.

The present application is also related to U.S. patent application Ser. No. 13/054,066, filed on Jan. 13, 2011, which is a 371 national stage application of PCT/GB2009/001760, filed on Jul. 15, 2009 and which, in turn, relies in Great Britain Application No. 0812864.7, filed on Jul. 15, 2008, for priority. Each of the aforementioned applications is hereby incorporated by reference in its entirety.

The present application is also related to U.S. patent application Ser. No. 13/063,467, filed on Mar. 11, 2011, which is a 371 national stage application of PCT/GB09/51178, filed on Sep. 13, 2009 and which, in turn, relies in Great Britain Application No. 0816823.9, filed on Sep. 13, 2008, for priority. Each of the aforementioned applications is hereby incorporated by reference in its entirety.

The present application is also related to U.S. patent application Ser. No. 13/032,593, filed on Feb. 22, 2011. Each of the aforementioned applications is hereby incorporated by reference in its entirety.

The present application is also related to U.S. patent application Ser. No. 12/787,930, filed on May 26, 2010, and which relies on U.S. Provisional Patent Application No. 61/181,068 filed on May 26, 2009, for priority. Each of the aforementioned applications is hereby incorporated by reference in its entirety.

The present application is also related to U.S. patent application Ser. No. 12/788,083, filed on May 26, 2010, and which relies on U.S. Provisional Patent Application No. 61/181,070 filed on May 26, 2009, for priority. Each of the aforementioned applications is hereby incorporated by reference in its entirety.

The present application is also related to U.S. patent application Ser. No. 13/086,708, filed on Apr. 14, 2011, which is a continuation of U.S. Pat. No. 7,949,101, filed on Jun. 16, 2009. Each of the aforementioned applications is hereby incorporated by reference in its entirety.

The present application is related to U.S. patent application Ser. No. 12/792,931, filed on Jun. 3, 2010, and which relies on U.S. Provisional Patent Application No. 61/183,591 filed on Jun. 3, 2009, for priority. Each of the aforementioned applications is hereby incorporated by reference in its entirety.

The present application is also related to U.S. patent application Ser. No. 13/346,705, filed on Jan. 9, 2012, which is a continuation of U.S. Ser. No. 12/835,682, filed on Jul. 13, 2010, and which relies on U.S. Provisional Patent Application No. 61/225,257 filed on Jul. 14, 2009, for priority. Each of the aforementioned applications is hereby incorporated by reference in its entirety.

The present application is also related to U.S. patent application Ser. No. 12/787,878, filed on May 26, 2010, and which relies on U.S. Provisional Patent Application No. 61/181,077 filed on May 26, 2009, for priority, which is:

1. A continuation-in-part of U.S. patent application Ser. No. 12/485,897, filed on Jun. 16, 2009, which is a continuation of U.S. patent application Ser. No. 10/554,656, filed on Oct. 25, 2005, and now issued U.S. Pat. No. 7,564,939, which is a 371 national stage application of PCT/GB04/01729, filed on Apr. 23, 2004 and which, in turn, relies on Great Britain Application No. 0309387.9, filed on Apr. 25, 2003, for priority;
2. A continuation-in-part of U.S. Pat. No. 7,903,789, filed on Feb. 16, 2009, which is a continuation of U.S. Pat. No. 7,512,215, filed on Oct. 25, 2005, which is a 371 national stage application of PCT/GB2004/01741, filed on Apr. 23, 2004 and which, in turn, relies on Great Britain Application Number 0309383.8, filed on Apr. 25, 2003, for priority;
3. A continuation-in-part of U.S. Pat. No. 7,664,230, filed on Oct. 25, 2005, which is a 371 national stage application of PCT/GB2004/001731, filed on Apr. 23, 2004 and which, in turn, relies on Great Britain Patent Application Number 0309371.3, filed on Apr. 25, 2003, for priority;
4. A continuation-in-part of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority;
5. A continuation-in-part of U.S. Pat. No. 7,929,663, filed on Apr. 12, 2010, which is a continuation of U.S. patent application Ser. No. 12/211,219, filed on Sep. 16, 2008, and now issued U.S. Pat. No. 7,724,868, which is a continuation of U.S. patent Ser. No. 10/554,655, filed on Oct. 25, 2005, and now issued U.S. Pat. No. 7,440,543, which is a 371 national stage application of PCT/GB2004/001751, filed on Apr. 23, 2004, and which, in turn, relies on Great Britain Patent Application Number 0309385.3, filed on Apr. 25, 2003, for priority;
6. A continuation-in-part of U.S. Pat. No. 8,085,897, filed on Jan. 29, 2010, which is a continuation of U.S. patent application Ser. No. 10/554,570, filed on Oct. 25, 2005, and now issued U.S. Pat. No. 7,684,538, which is a 371 national stage application of PCT/GB2004/001747, filed on Apr. 23, 2004, and which, in turn, relies on Great Britain Patent Application Number 0309379.6, filed on Apr. 25, 2003, for priority;
7. A continuation-in-part of U.S. Pat. No. 7,876,879, issued on Jan. 25, 2011 and U.S. patent application Ser. No. 12/142,005, filed on Jun. 19, 2008, both of which are 371 national stage applications of PCT/GB2006/004684, filed on Dec. 15, 2006, which, in turn, relies on Great Britain Patent Application Number 0525593.0, filed on Dec. 16, 2005, for priority;
8. A continuation-in-part of U.S. patent application Ser. No. 13/313,854, filed on Dec. 7, 2011, which is a continuation of U.S. patent application Ser. No. 12/478,757, filed on Jun. 4, 2009, now issued U.S. Pat. No. 8,094,784, which is a continuation of U.S. patent application Ser. No. 12/364,067, filed on Feb. 2, 2009, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority. In addition, U.S. patent application number relies on Great Britain Patent Application Number 0812864.7, filed on Jul. 15, 2008, for priority; and 9. A continuation-in part of U.S. patent application Ser. No. 12/712,476, filed on Feb. 25, 2010, which relies on U.S. Provisional Patent Application No. 61/155,572 filed on Feb. 26, 2009 and Great Britain Patent Application No. 0903198.0 filed on Feb. 25, 2009, for priority.

Each of the aforementioned PCT, foreign, and U.S. applications, and any applications related thereto, is herein incorporated by reference in their entirety.

FIELD

The present specification relates to X-ray scanning and, in particular, to the improved reconstruction of images generated by a computed tomography (CT) X-ray scanning system.

BACKGROUND

Three-dimensional images of the interior of objects are currently generated, using conventional X-ray systems, for a variety of purposes, including security inspection, medical diagnostics, process imaging and non-destructive testing. Several different system configurations currently exist for generating the image scanning data which is used to create the three-dimensional images.

In one exemplary system, X-ray source is rotated about the object under inspection. A collimated fan-beam of X-rays from the source passes through the object under inspection to a one-dimensional array of X-ray detectors located on the opposite side of the object from the source. Transmission X-ray data is collected at each of a number of angles to form a two-dimensional sinogram. This information is passed through an image reconstruction algorithm to create a two-dimensional cross-sectional image of the object under inspection.

In another exemplary system, an X-ray source emits X-rays into a cone of radiation which passes through the object to a two-dimensional array of X-ray detectors which are directly opposed to the source. The source and detector array are rotated about the object under inspection and the resulting X-ray projection data is reconstructed into a three-dimensional image.

In another exemplary system, the object being inspected is translated along a substantially linear trajectory, while the source and detector assembly rotate in a plane perpendicular to the axis of object motion, to form an improved three-dimensional image. In this case, the source describes a helical motion about the object, the locus of source point being situated on the surface of a cylinder about the object. The rate at which the object moves through the plane of the source and detectors is related to the rate at which the source and detector assembly rotate about the object, this ratio being described as the pitch of the helix.

Applicant has developed a new generation of X-ray systems that implement X-ray sources with more than one electron gun and one or more high voltage anodes within a single vacuum envelope. In this system, an X-ray source allows non-sequential motion of an X-ray beam about an object under inspection through the use of multiple grid controlled electron guns which can be excited in any chosen sequence, the electron beam from each source being directed to irradiate anode sections which are distributed around the object under inspection. This allows non-helical source trajectories to be described at high speeds consistent with the requirements for dynamic and high-throughput object imaging. Additionally, the rapid switching of electron guns under electrostatic control enables the fast movement of the effective focal spot of the X-ray tube and the rapid generation of sets of tomographic X-ray scan data without the use of moving parts.

By configuring the firing sequence of the electron guns appropriately, an optimal set of X-ray projection data can be collected at rates far higher than in conventional systems. Examples of such systems are disclosed in the applications which are listed above and incorporated herein by reference.

While Applicant has previously described an approach to sequentially firing the electron guns, there is a need to develop an improved method of optimally firing the sequence of electron guns to avoid the creation of image artifacts.

In particular, Applicant has recognized that the conventional helical motion of the X-ray source results in a sub-optimal sampling of the projection space within the object with the consequent formation of image artifact due to this limited sampling. Applicant has further recognized that, through the use of multi-emitter X-ray source technology, an optimal source firing sequence can be determined which does not represent a helical scanning geometry and which would result in the generation of improved three-dimensional images.

SUMMARY

In one embodiment, the present specification discloses an X-ray imaging apparatus for obtaining a radiation image of an object having a length, comprising: a plurality of X-ray tubes arranged in a first ring around the object, each X-ray tube comprising a predefined number of X-ray sources, each X-ray source being equally spaced from an adjacent source, each X-ray source emitting X-rays during a predefined emission period; and a controller configured to cause each of said X-ray sources to emit X-rays in accordance with a firing pattern, wherein said firing pattern causes a substantially even distribution of X-rays from the X-ray sources over a surface of a virtual cylinder, having a length, wherein the virtual cylinder is positioned around the object and the length of the virtual cylinder is equal to or greater than the length of the object. The X-ray sources are stationary.

Optionally, the length of the virtual cylinder is equal to the length of the object plus a distance, wherein said distance is within a range of 0 mm to 100 mm. The firing pattern causes the X-ray sources to emit X-rays in a non-sequential order. The firing pattern causes the X-ray sources to emit X-rays in a non-helical pattern. The firing pattern is rotationally invariant.

Optionally, the X-ray imaging apparatus defines a reconstruction volume comprising a plurality of voxels, wherein X-rays intersect each voxel of the reconstruction volume at a plurality of angles and wherein said plurality of angles are substantially evenly distributed over a range of 0 degrees to 360 degrees. The X-ray imaging apparatus further comprises a plurality of sensors arranged in a second ring around the object for detecting X-rays emitted from the plurality of X-ray sources after passing through the object, wherein the sensors are offset from the X-ray sources along a predefined axis.

In another embodiment, the present specification discloses an X-ray imaging apparatus for obtaining a radiation image of an object having a length, comprising: a plurality of X-ray tubes, each X-ray tube comprising a predefined number of X-ray sources and each X-ray source emitting X-rays during a predefined emission period, wherein the X-ray sources are arranged in a circular pattern on a plane that is normal to a direction of travel of the object; and a controller configured to cause each of said X-ray sources to emit X-rays in accordance with a firing pattern, wherein said firing pattern causes said sources to fire in a sequence that is rotationally invariant. During operation, the X-ray tubes are stationary.

Optionally, the object travels on a conveyor belt having a speed in a range of 250 mm/s to 500 mm/s. The firing pattern causes an even distribution of X-rays from the X-ray sources over a surface of a virtual cylinder, having a length, wherein the virtual cylinder is positioned around the object and the length of the virtual cylinder is equal to or greater than the length of the object. The length of the virtual cylinder is equal to the length of the object plus a distance, wherein said distance is within a range of 0 mm to 100 mm.

Optionally, the X-ray imaging apparatus further comprises a plurality of detectors for generating projection data, wherein the controller modifies the firing pattern based upon said projection data. Optionally, the X-ray imaging apparatus further comprises a plurality of detectors for generating projection data, wherein the sources and detectors, taken in combination, exhibit multi-fold symmetry.

In another embodiment, the present specification discloses an X-ray imaging apparatus defining a reconstruction volume, comprising a plurality of voxels, for scanning an object, comprising a plurality of X-ray tubes, each X-ray tube comprising a predefined number of X-ray sources and each X-ray source emitting X-rays during a predefined emission period, wherein, during operation, the X-ray sources are stationary and wherein the X-ray sources are positioned in a plane; a plurality of detectors, wherein the detectors are on at least one plane that is parallel to the plane of the sources and for which the detectors and the sources are not co-planar and wherein the detectors generate projection data; and a controller configured to cause each of said X-ray sources to emit X-rays in accordance with a firing pattern, wherein said firing pattern causes the X-ray sources to emit X-rays that intersect each voxel of the reconstruction volume at a plurality of angles and wherein said plurality of angles are substantially evenly distributed over a range of 0 degrees to 360 degrees.

Optionally, the firing pattern causes an even distribution of X-rays from the X-ray sources over a surface of a virtual cylinder, having a length, wherein the virtual cylinder is positioned around the object and the length of the virtual cylinder is equal to or greater than the length of the object. The length of the virtual cylinder is equal to the length of the object plus a distance, wherein said distance is within a range of 0 mm to 100 mm. The data storage requirements for an implementation of reconstruction methods using the projection data are less than data storage requirements for an implementation of reconstruction methods using projection data generated from sequential or helical firing patterns. The computational processing power requirements for an implementation of reconstruction methods using the projection data are less than computational processing power requirements for an implementation of reconstruction methods using projection data generated from sequential or helical firing patterns.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings, wherein:

FIG. 7($a$) illustrates a first plot of a sampling pattern using a helical geometry;

FIG. 7($b$) illustrates a second plot of a sampling pattern using a firing pattern produced by methods disclosed in the present application.

DETAILED DESCRIPTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
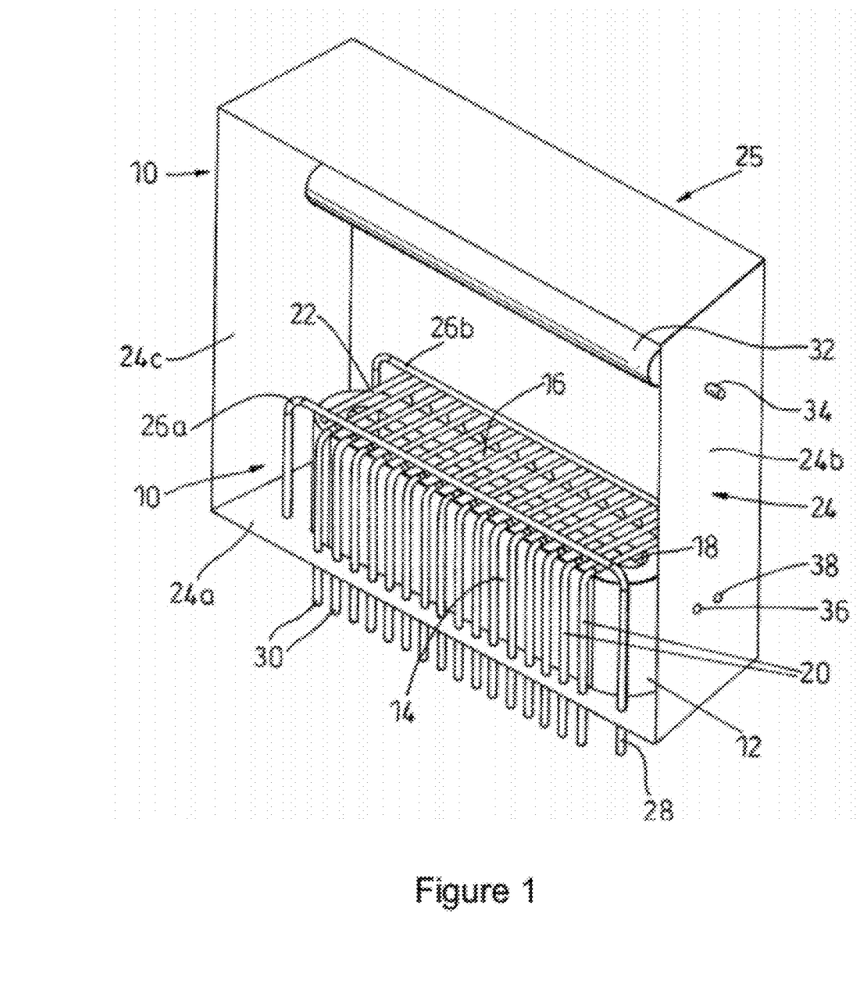
FIG. 1 shows an X-ray emitter suitable for use with the invention.

FIG. 1 shows a multi-emitter X-ray source 10 in which an anode 32 is irradiated by a set of electron guns 18, the whole assembly being located within a vacuum envelope 25. Each electron source is controlled by an electrical potential which is applied to the electron gun assembly through a series of control pins 30. A common focus potential 28 can control the focal spot of each electron gun the tube to balance spatial resolution in an image against thermal loading of the anode. One skilled in the art shall recognize that alternative electron gun arrangements may be configured to selectively irradiate regions of an anode and all such embodiments are covered within the scope of this application.

The multi-focus X-ray tube 10 comprises a ceramic former 12 and the electron guns, or emitter elements, 18 extending along between the sides 14, 16 of the former. A number of grid elements in the form of grid wires 20 are supported on the former 12 and extend over the gap between its two sides 14, 16 perpendicular to the emitter elements 18, but in a plane which is parallel to it. A number of focusing elements in the form of focusing wires 22 are supported in another plane on the opposite side of the grid wires to the emitter elements. The focusing wires 22 are parallel to the grid wires 20 and spaced apart from each other with the same spacing as the grid wires, each focusing wire 22 being aligned with a respective one of the grid wires 20.

The source 10 is enclosed in a housing 24 of an emitter unit 25 with the former 12 being supported on the base 24a of the housing. The focusing wires 22 are supported on two support rails 26a, 26b which extend parallel to the emitter elements 18, and are spaced from the former 12, the support rails being mounted on the base 24a of the housing. The support rails 26a, 26b are electrically conducting so that all of the focusing wires 22 are electrically connected together. One of the support rails 26a is connected to a connector 28 which projects through the base 24a of the housing to provide an electrical connection for the focusing wires 22. Each of the grid wires 20 extends down one side 16 of the former and is connected to a respective electrical connector 30 which provide separate electrical connections for each of the grid wires 20.

An anode 32 is supported between the side walls 24b, 24c of the housing. The anode extends parallel to the emitter elements 18. The grid and focusing wires 20, 22 therefore extend between the emitter elements 18 and the anode 32. An electrical connector 34 to the anode extends through the side wall 24b of the housing.

The emitter elements 18 are supported in the ends of the former and are heated by means of an electric current supplied to it via further connectors 36, 38 in the housing.

In order to produce a beam of electrons from one position, a pair of adjacent grid wires 20 can be connected to an extracting potential which is positive with respect to the elements 18 while the remaining grid wires are connected to a blocking potential which is negative with respect to the element 18. By selecting which pair of wires 20 is used to extract electrons, the position of the beam of electrons can be chosen. As the X-rays will be emitted from the anode 32 at a point where the electrons strike it, the position of the X-ray source can also be chosen by choosing the extracting pair of grid wires. The focusing elements 22 are all kept at a positive potential with respect to the grid wires 20 so that electrons extracted between any pair of the grid wires will also pass between, and be focused by, a corresponding pair of focusing elements 22.

Figure 2:
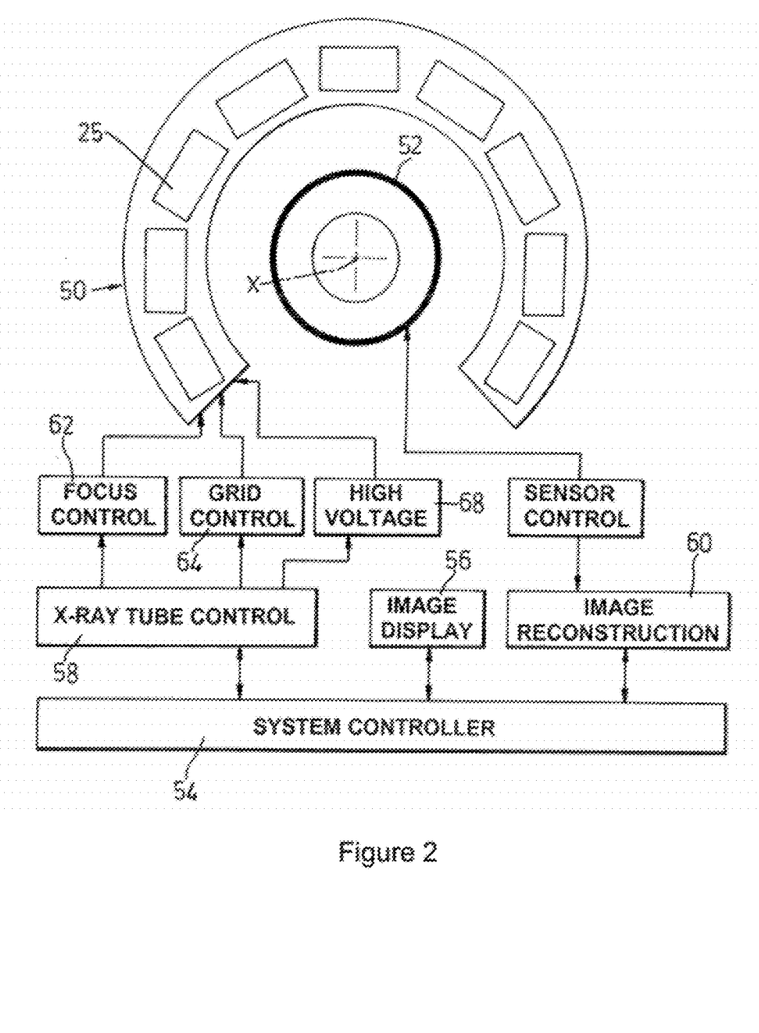
FIG. 2 is a diagram of an X-ray imaging system according to the invention including a number of emitter units as shown in FIG. 1.

FIG. 2 shows a suitable control system for a multi-emitter X-ray tube based X-ray imaging system in which precise timing is maintained between the grid control system (which determines the region of the anode to be irradiated) and acquisition of data from the X-ray sensor array. An image reconstruction engine combines the two-dimensional projection data into a three-dimensional data set for operator inspection.

An X-ray scanner 50 is set up in a conventional geometry and comprises an array of emitter units 25 arranged in an arc around a central scanner axis X, and orientated so as to emit X-rays towards the scanner axis X. A ring of sensors 52 is placed inside the emitters, directed inwards towards the scanner axis. The sensors 52 and emitter units 25 are offset from each other along the axis X so that X-rays emitted from the emitter units pass by the sensors nearest to them, through the object, and are detected by a number of sensors furthest from them. The number of sensors 52 that will detect X-rays from each source depends on the width of the fan of X-rays that is emitted from each source position in the tubes 25. The scanner is controlled by a control system which operates a number of functions represented by functional blocks in FIG. 2.

A system control block 54 controls, and receives data from, an image display unit 56, an X-ray tube control block 58 and an image reconstruction block 60. The X-ray tube control block 58 controls a focus control block 62 which controls the potentials of the focus wires 22 in each of the emitter units 25, a grid control block 64 which controls the potential of the individual grid wires 20 in each emitter unit 25, and a high voltage supply 68 which provides the power to the anode 32 of each of the emitter blocks and the power to the emitter elements 18. The image reconstruction block 60 controls and receives data from a sensor control block 70 which in turn controls and receives data from the sensors 52.

In operation, an object to be scanned is passed along the axis X, and X-ray beams are directed through the object from the X-ray tubes 25. In each scanning cycle each source position in each tube 25 is used once, the scanning cycle being repeated as the object moves along the axis X. Each source position produces a fan of X-rays which after passing through the object are detected by a number of the sensors 52.

In prior applications, Applicant described the order of X-ray emission from the source positions in the tubes 25 as being chosen so as to minimize the thermal load on the X-ray tube. This was achieved by ordering the emissions so that each source position is non-adjacent to, and therefore spaced from, the previous one and the subsequent one. As described below, the present specification discloses an improved approach to ordering X-ray emissions from the source positions in the tubes 25.

Figure 3:
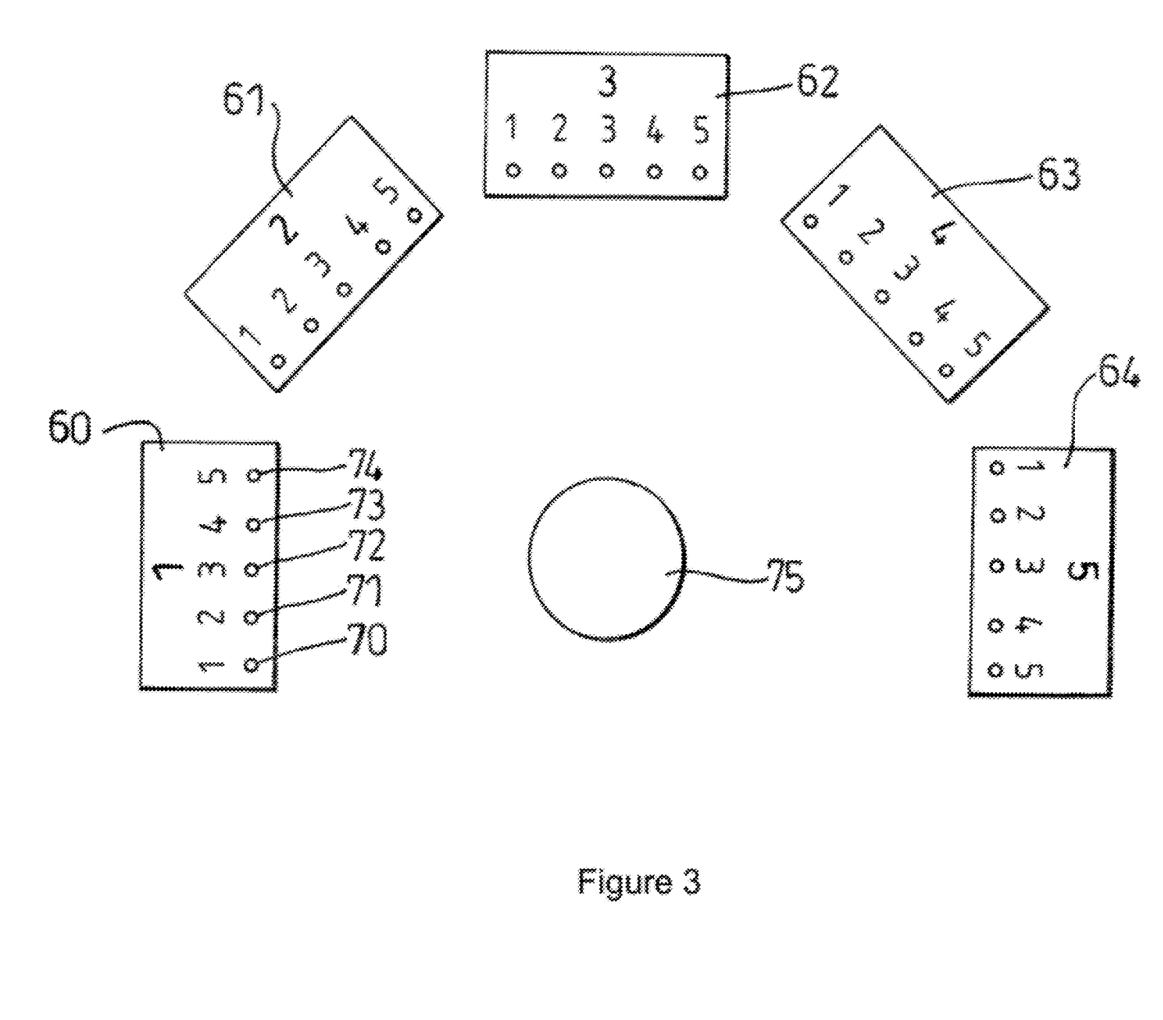
FIG. 3 is a diagram of the layout of an X-ray imaging system according to a second embodiment of the invention.

Various configurations of X-ray imaging system are covered within the scope of this application. For example, FIG. 3 shows a system in which an object reconstruction space, defined by region 75, is irradiated by a series of linear X-ray tube sections 60, 61, 62, 63, 64, each of which contain a series individual X-ray source emission points, i.e. 70, 71, 72, 73, 74. The sources in each X-ray tube, labeled 1, 2, 3, 4, 5, can then be fired in a predefined sequence.

Figure 4:
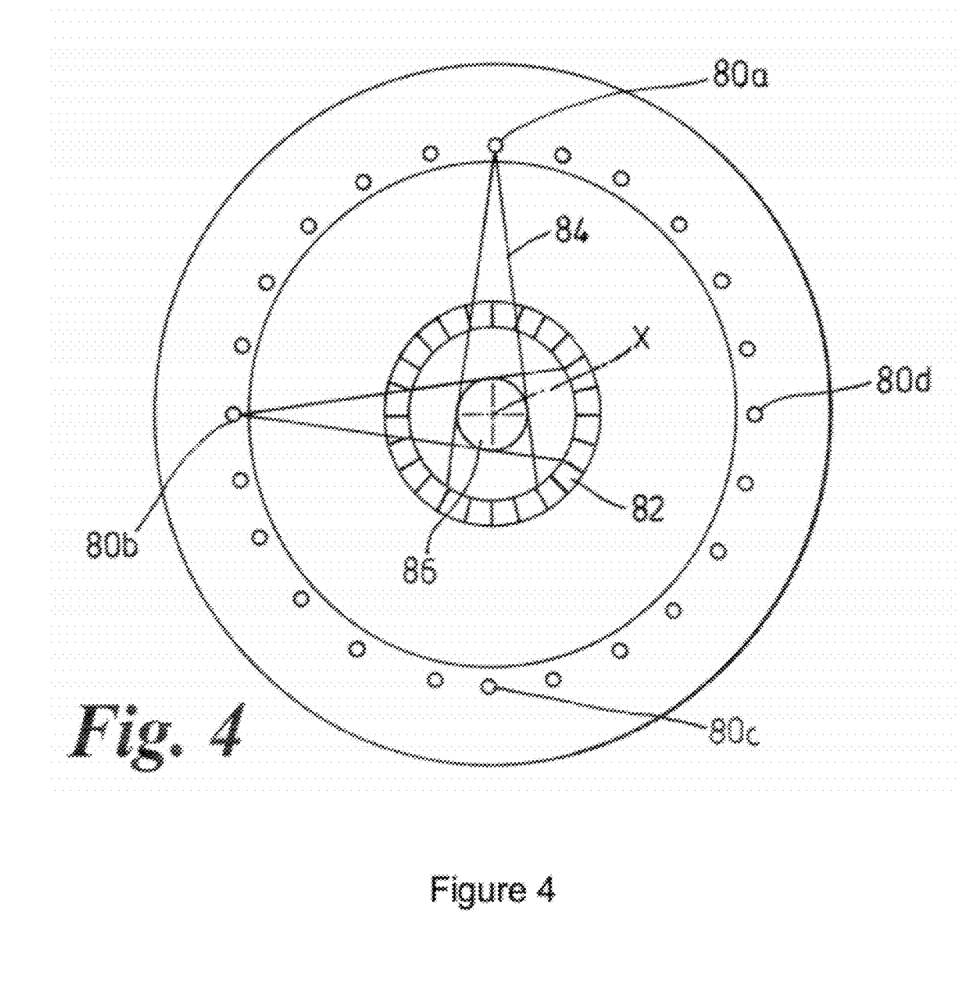
FIG. 4 is a diagram of the layout of an X-ray imaging system according to a third embodiment of the invention.

FIG. 4 shows a system configuration where the image reconstruction region 86 is surrounded by an array of source points 80 with a ring of detectors 82 being located in a plane adjacent to the plane of the source points. The X-ray sources 80 are spaced around an axis X, with the sensors 82 axially offset from the sources 80. When one of the sources 80a emits an X-ray beam 84 this diverges, passes through the object 86 and reaches a number of the sensors 82. When the sensors 82 which are needed to detect X-rays from each of the source positions 80 are known, source positions can be selected which can emit simultaneously, provided that they do not require any common detectors. For example if there are 24 source positions 80 and 24 sensors 82 and each source position requires 5 sensors, then four of the sensors 80a, 80b, 80c, 80d, spaced around the object at 90° intervals can be used simultaneously.

In the present application, a computed tomography system having non-rotating X-ray sources is programmed to optimize the source firing pattern. In one embodiment, the CT system is a fast cone-beam CT scanner which uses a fixed ring of multiple sources and fixed rings of detectors in an offset geometry. It should be appreciated that the source firing pattern is effectuated by a controller, having a processor and memory for storing a plurality of programmatic instructions. The instructions are programmed to implement the source firing pattern methods disclosed herein. When the processor executes the instructions, the controller causes the X-ray sources to fire in accordance with the determined source firing pattern.

Figure 5:
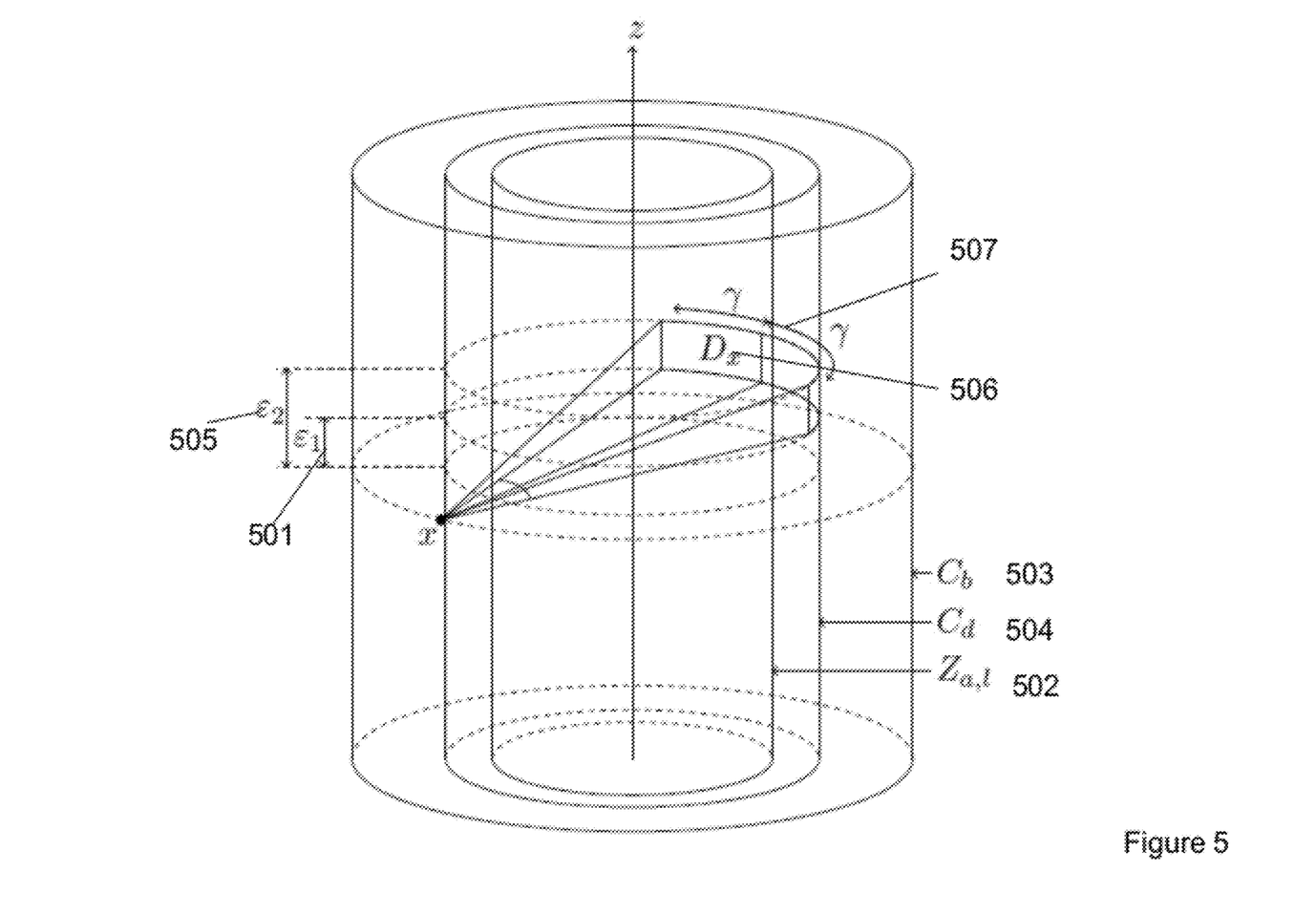
FIG. 5 illustrates an exemplary geometry of a real time tomography (RTT) system.

It should further be appreciated that a computed tomography system having non-rotating X-ray sources provides certain benefits, including improved scan time since time sinks caused by the physical rotation of the source around the object being scanned are eliminated. However, since the X-ray source and detector geometry are offset in the z-direction by some distance $\epsilon_1$ 501, as shown in FIG. 5, image reconstruction methodologies used in conventional rotating gantry CT systems cannot be applied to this geometry. Methods to determine a source firing pattern, adapted to geometries where the X-ray sources and detector geometry are offset, are therefore required.

Referring to FIG. 5, $Z_a$ and $C_a$ represent respectively the cylinder of radius 'a' with axis along the z-axis, and its boundary. The function f, representing the object, is assumed to be supported on $Z_{a,1}$ 502—a subset of Za of some finite length l and centered at the origin. The sets of possible source and detector positions are given by $C_b$ 503 and $C_d$ 504 respectively, where a<d<b. Let $\epsilon_2 > \epsilon_1 > 0$ represent the source-detector offsets in the z direction; then relative to some source position $x \in C_b$, the active detector region $D_x$ 506 is the subset of $C_d$ defined by $\epsilon_1$ 501, $\epsilon_2$ 505 and the angular extents $-\gamma, \gamma$ 507.

The geometry is assumed to be shift-invariant, so that the active detector region is the same viewed from the perspective of any source position $x \in Cb$. Considering an arbitrary $x \in Cb$, let $\Pi\alpha,x$ be a plane containing x, and intersecting the transaxial plane containing x in a line tangent to Cb at x. This plane has equation y. $\alpha=s$, for some $s \in R$ and $\alpha \in S^2$, the unit 2-sphere. Let L $\alpha,x$ be the line in $\Pi\alpha,x$ intersecting x and the z-axis. One may assume that the offsets $\epsilon_1, \epsilon_2$ are defined such that for any $x \in Cb$, there exists $\alpha \in S^2$ such that all rays in the plane $\Pi\alpha',x$, intersecting the support of f and parallel to $L\alpha',x$, for $\alpha'$ in some arbitrary small neighbourhood of $\alpha$, are measured.

Accordingly, source point x lines in a plane which is separated from the lower edge of a two-dimensional array of detectors by a distance $\epsilon_1$ and from the upper edge of the same detector array by a distance $\epsilon_2$. The section of the detector array extends away from the plane intersecting the axis of rotation and the center of the scan zone by a distance of $\pm\Gamma$ 507. The source occupies points on the surface of a cylinder $C_b$ 503 while the detectors are on the surface of a cylinder $C_d$ 504. The object is contained within a cylinder $Z_{a,1}$ 502. The object moves along axis z during a scan.

In one embodiment, system executes an optimal source firing sequence which provides uniform sampling of the projection space within the object, thereby resulting in minimal image artifact. Here, the system applies a constraint to require uniform sampling of the projection space. This is summarised in the following equation:

$$\Phi(i)=(k(i-1) \bmod N_s)+1 \qquad (1)$$

where $N_s$=number of sources in the system, k=increment between firing sources, and i=projection number. Note that k=1 for a helical scan.

Figure 6:
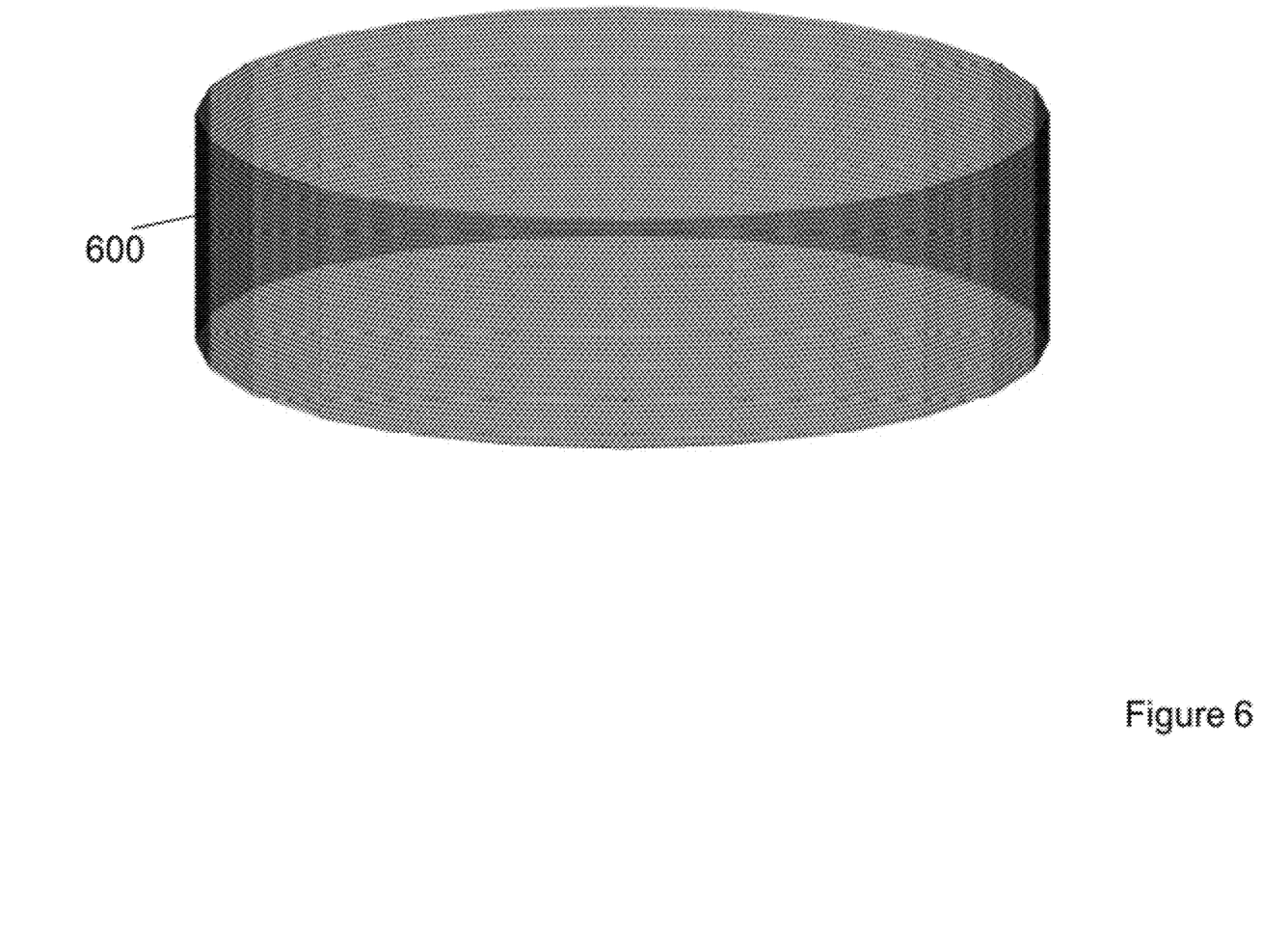
FIG. 6 illustrates the source positions on a regular lattice on the surface of a cylinder.

To find the optimal value of k, the objective is to fit the surface of the cylinder $C_b$ 503 with a uniformly distributed triangulated mesh of source points 600, such as that shown in FIG. 6. Here, a suitable set of equations for calculating k are $$l_1^2 = d^2 + \left(\frac{k^{-1}p_z}{N_s}\right)^2 \qquad (2)$$

$$l_2^2 = (2d)^2 + p_z^2\left(\frac{2k^{-1}}{N_s} - 1\right)^2 \qquad (3)$$

$$l_3^2 = d^2 + p_z^2\left(1 - \frac{k^{-1}}{N_s}\right)^2 \qquad (4)$$

where d is the distance between adjacent sources, $p_z$ is the z pitch, $k^{-1}$ is the inverse of k modulo $N_s$ and $l_1, l_2$ and $l_3$ are the lengths of the three side of each triangle.

In order to make the lattice triangles as equilateral as possible, the value of $k^{-1}$ is chosen to minimise the standard deviation of $l_1, l_2$ and $l_3$. The value of k is then chosen to make $k^{-1}$ as close as possible to this value, since not all values of k have an inverse modulo $N_s$.

More specifically, where the system has a set of discrete sources denoted by $S=s_1, \ldots s_S$, a firing order of period 1 revolution can be defined as the periodic extension of the sequence $\ldots, \Phi(1), \ldots, \Phi(S); \ldots$, which is determined by some function $\Phi: \{1, \ldots, S\} \rightarrow \{1, \ldots S\}$.

This definition may be generalized to cover firing orders of an arbitrary period, R, revolutions. As stated above, the firing order determines the sequence in which the physical sources in the RTT system are switched on and off. For a particular firing order $\Phi$, as i runs from 1 to S, the sources $s_{\Phi(1)}, \ldots, s_{\Phi(S)}$ are switched in sequence.

While not required, it is preferable to construct a firing pattern that makes use of all sources, i.e. firing orders where the function $\Phi$ is bijective (i.e. permutations of $\{1, \ldots, S\}$. This ensures all sources are used and justifies the use of the term revolution, since a full set of projections from the physical sources $s_1, \ldots s_S$ is conceptually analogous to, but substantially technically different from, a complete revolution of the gantry of a conventional CT scanner. Given this restriction, and the assumption that the firing order has period 1 revolution, without loss of generality, one can adopt the convention that for any firing order, $\Phi(1)=1$.

For an RTT system with S sources, the firing order defined by the function $\Phi$ is said to be order-1 rotationally invariant if for some fixed integer k we have:

$$\Phi(i) \equiv (\Phi(i+1)-k)(\bmod |S|), \forall i=1, \ldots, |S| \qquad (5)$$

Interpreting this geometrically, this means that, from the perspective of some source $s_i$, if the system moves to source $s_{i+1}$, the positions of all other sources in three-dimensional space, relative to the source one is at, does not change. Stated differently, a system is rotationally invariant if it has multi-fold symmetry. In an exemplary application, a system has a configuration of detectors and sensors that exhibit 24 fold symmetry.

An order-1 rotationally invariant firing order is given by a function $\Phi$ of the form:

$$\Phi(i)=(k(i-1) \bmod |S|)+1; \qquad (6)$$

where k is some integer co-prime to jSj, and is always of period 1 revolution.

A special case of the order-1 rotationally invariant firing order is the sequential firing order. It is the period 1 firing order defined simply by the identity mapping fi(i)=i, giving a classical single helical source trajectory.

Higher order rotationally invariant firing orders are necessarily defined over periods of greater than one revolution, and can be viewed as a generalization of the order-1 case above, where the integer k is chosen such that gcd $(k;N_S)>1$. If m=gcd $(k;N_S)$ then the sequence created by (5) repeats every $N_S/m$ sources. In order to avoid this, a second increment q, is introduced that is coprime to k and that gets added every $N_S/m$ sources. If q=1, this can be expressed by functions $\Phi_r$, for $1 \leq r \leq N_S/m$, defined as follows $$\Phi r(i)=[(k(i-1)+m(r-1)+[((i-1)m/NS)]) \bmod NS)+1; \qquad (7)$$

where [.] is the round towards negative infinity operator. Such a firing order is often referred to as a multi-helix, since it can be viewed as defining helical trajectories for multiple sources.

The choice of firing order is dictated to a certain extent by the reconstruction algorithm implemented. If an analytical algorithm is used that assumes some choice of source trajectory, then the firing pattern should approximate that trajectory. In order to consider the problem of optimizing the firing order in full generality, a method is required that is independent of the choice of firing order.

In one embodiment, a firing order is selected that creates an evenly spaced sampling lattice on the surface of a virtual cylinder. The virtual cylinder preferably defines a distance which exceeds the length of the object being scanned, plus sufficient length to allow the data collection apparatus to cover all points in the object. In one embodiment, the virtual cylinder has a length equal to the length of the object plus an additional distance, such as 10, 50, or 100 mm or any increment therein. In a preferred embodiment, using a coordinate system where zero is the center point of the virtual cylinder, the cylinder's length is equal to the length of the object +/−50 mm. The firing pattern is optimized such that even source coverage of the cylinder surface is achieved, namely that the distance between points on the cylinder surface are of equal length for as far as possible between adjacent source points in all directions. Preferably, the even source coverage applies to the full length of the virtual cylinder. With order-1 rotationally invariant firing orders of the form (5), a firing order can be constructed that gives close to an equilateral triangle sampling lattice on the surface of the cylinder.

Preferably, the firing order is chosen to get an even distribution of the angles of the X-rays intersecting each voxel of the reconstruction volume over a range of 360 degrees and along the length of the object. Here, the angle is taken to mean the angle of the detector relative to the source, in the projection of the X-ray onto a transaxial plane. For example, for a system with 768 sources, a firing order that satisfies both of these properties is given by substituting k=35 in (4).

Figure 7A:
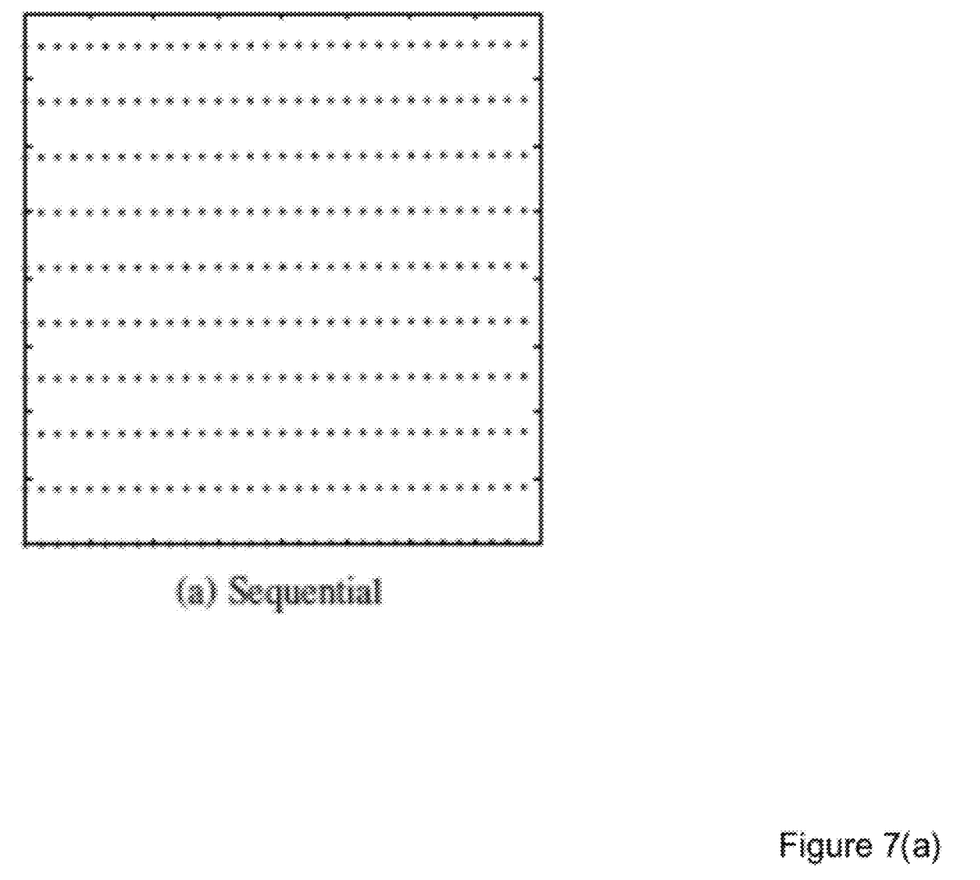
Figure 7B:
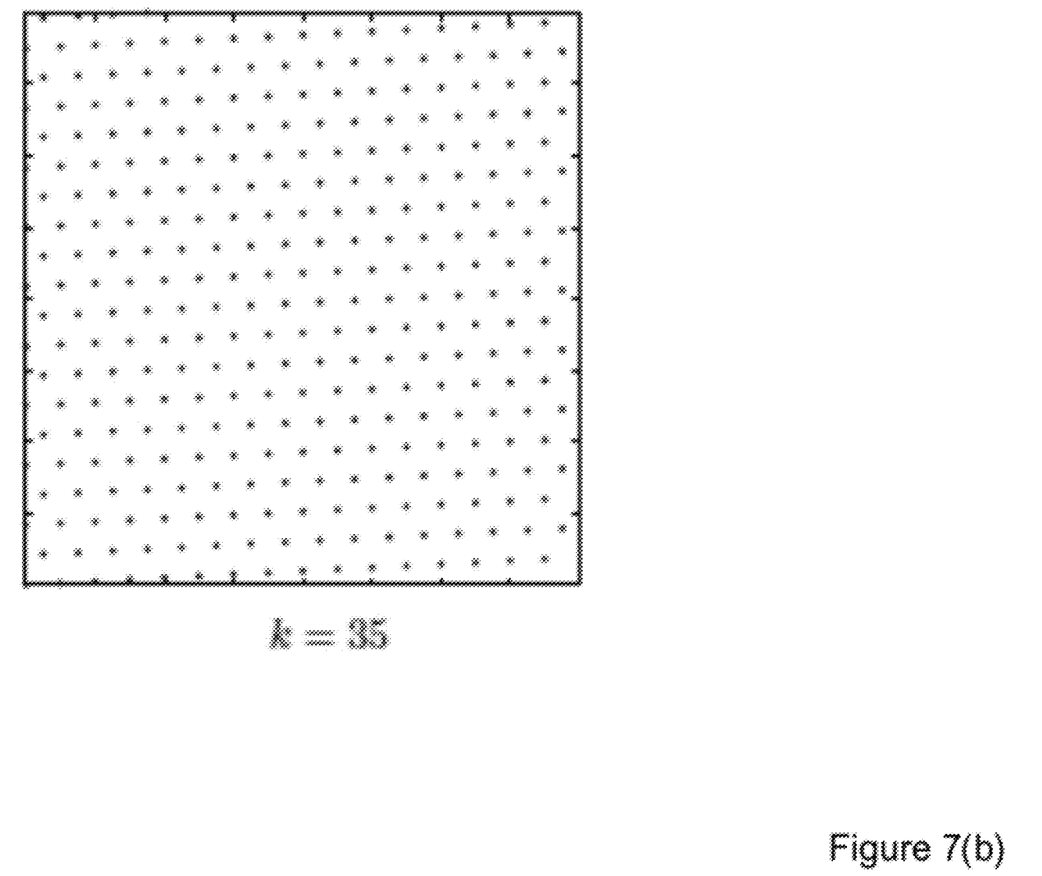

A section of source point positions on the surface of the cylinder Cb is shown in FIGS. 7(a) and (b). FIG. 7(a) shows that the set of source points when k=1, i.e. a conventional helical scan firing pattern, describe lines across the surface, showing that large regions of the surface are not covered. In contrast, FIG. 7(b) shows a triangular mapped array of source points which, for the system modeled, uses a k value source increment of 35.

Figure 8:
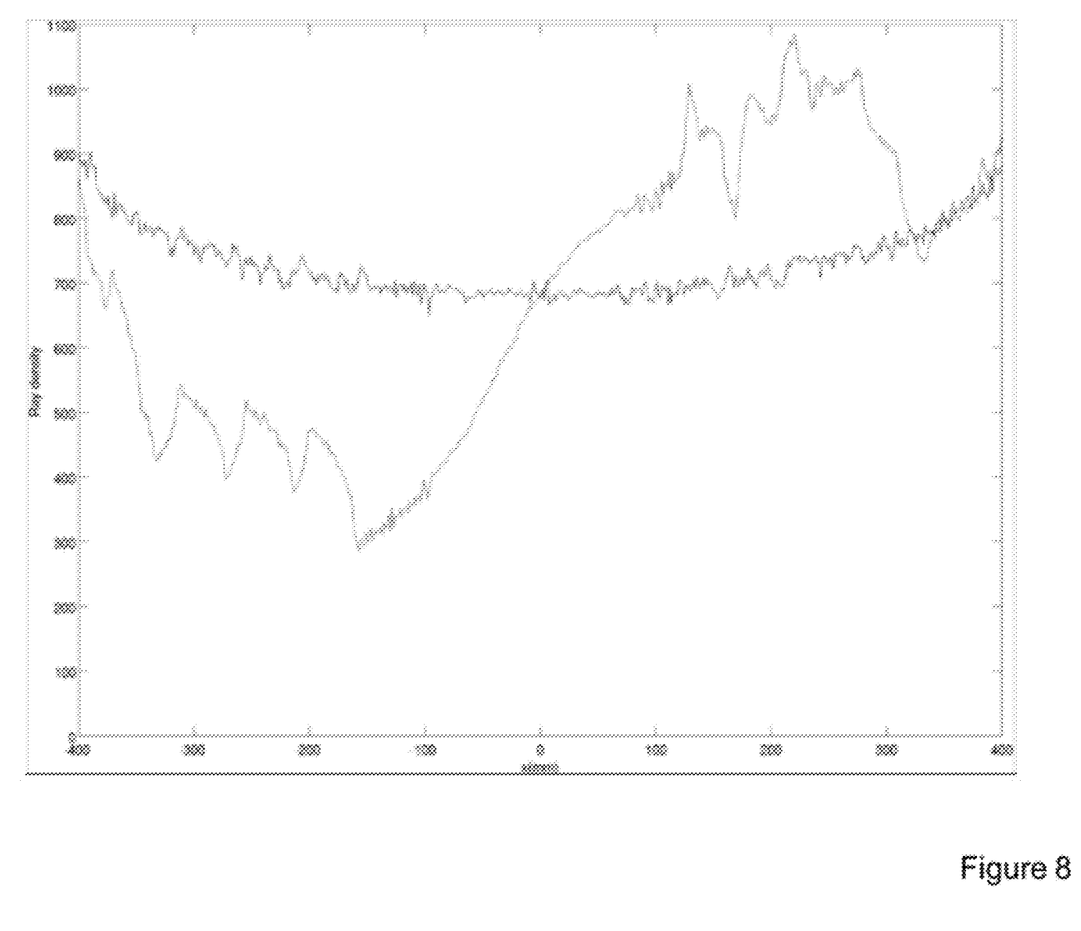
FIG. 8 shows graphs of profiles of projection densities for different firing patterns.

To understand the practical impact of this non-helical source trajectory, consider the data shown in FIG. 8, which depicts profiles of projection density along one line through the object (a line at the center of the projection volume perpendicular to the z-axis) with no object in the beam. Graph 805 shows a profile through the projection line density for a standard helical scan geometry, which demonstrates a considerable non-uniformity of projection density and leads to reconstructed image artifact, such as streaking. In contrast, graph 810 shows a much more uniform projection density, obtained using the methods described herein, which produces a significantly cleaner reconstructed image with little artifact due to error in sampling the projection data.

Additionally, an optimizing firing pattern, in accordance with the methods disclosed herein, enable an improved implementation of reconstruction methods and, more particularly, minimizes data storage requirements and/or computational processing power requirements for the implementation of certain reconstruction algorithms, such as ART, methods that solves a set of linear equations, iterative linear equation solvers, or any other reconstruction method that directly solves a system of equations, on projection data generated by the firing patterns disclosed herein relative to conventional firing patterns, such as sequential or helical patterns.

The presently disclosed methodologies have a number of advantages. First, the accuracy of any image reconstruction algorithm depends critically on the uniformity of projection density. By way of example, an algebraic reconstruction method is only as good as the equations which are available to it. A uniformly sampled projection space gives the best possible set of equations for an algebraic reconstruction, thereby enabling the generation of high quality three dimensional images at high scan rates. For example, where the CT system having stationary X-ray sources is configured as a bag or cargo scanner having a moving conveyor belt integrated therein, high quality three dimensional images can be generated even where the conveyor belt speed is faster than 200 mm/s, such as 250 mm/s or 500 mm/s.

Second, the source firing order may be changed in direct response to the measured projection data. For example, in the detection of a thin sheet of explosive material, X-ray attenuation along the length of the sheet is much greater than X-ray attenuation through the thickness of the sheet. Thus, the projection density in directions close to the long edge of the sheet can be advantageously increased, if necessary at the expense of projections through the plane of the sheet.

Third, a scanning system may be provided with multi-pass capability in which a first scan is conducted of the object with the evenly distributed source firing pattern disclosed herein with further scans being conducted with revised source firing trajectories to mitigate for regions of exceptional X-ray attenuation in order to balance the projection density of the scan overall. Accordingly, the source firing pattern for a given scan may be dynamically modulated based upon image data obtained from a prior scan.

Fourth, an X-ray scanning system may be constructed with a set of sources and detectors that are chosen to exhibit multi-fold radial symmetry. Here, uniform sampling can still be achieved, but the image reconstruction process is simplified through the use of small sets of coefficients which are re-used multiple times, once for each symmetry order.

Fifth, one can avoid having scanned regions with very high and very low X-ray density, which typically occurs with a sequential firing order or helical pattern. Where feed rates are sufficiently high, these regions could actually create a nullspace. However, for a firing order optimized as described herein, the distribution of X-ray density is much more even and the distribution of the angles of the X-rays intersecting the region is also more even. With the sequential firing order, there are regions within the reconstruction volume that are only illuminated from a very narrow range of angles. With the optimized firing order described herein, the distribution of the angles of the X-rays intersecting the region is more even, thereby resulting in fewer limited angle type artifacts in the data reconstructions.

In sum, for a CT scanner using switched sources and an offset detector geometry, the conventional helical source trajectory is far from optimal. Superior results are obtained using a firing order giving an even lattice sampling of source points on the surface of a cylinder.

The above examples are merely illustrative of the many applications of the system of present invention. For example, while a system with 768 sources has a k=35, it should be appreciated that systems with 384, 450 or 900 sources would have different k values, i.e. a 384 source system may optimally have a k value of 25, depending upon the angular distribution, or z pitch, of sampling. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An X-ray imaging apparatus for obtaining a radiation image of an object having a length, comprising:
 a plurality of X-ray tubes arranged in a first ring around the object, each X-ray tube comprising a predefined number of X-ray sources, each X-ray source being equally spaced from an adjacent source, each X-ray source emitting X-rays during a predefined emission period; and
 a controller configured to cause each of said X-ray sources to emit X-rays in accordance with a firing pattern, wherein said firing pattern causes a substantially even distribution of X-rays from the X-ray sources over a surface of a virtual cylinder, having a length, wherein the virtual cylinder is positioned around the object and the length of the virtual cylinder is equal to or greater than the length of the object.

2. The X-ray imaging apparatus of claim 1 wherein the length of the virtual cylinder is equal to the length of the object plus a distance, wherein said distance is within a range of 0 mm to 100 mm.

3. The X-ray imaging apparatus of claim 1 wherein the X-ray sources are stationary.

4. The X-ray imaging apparatus of claim 1 wherein the firing pattern causes the X-ray sources to emit X-rays in a non-sequential order.

5. The X-ray imaging apparatus of claim 1 wherein the firing pattern causes the X-ray sources to emit X-rays in a non-helical pattern.

6. The X-ray imaging apparatus of claim 1 wherein the firing pattern is rotationally invariant.

7. The X-ray imaging apparatus of claim 1 wherein the X-ray imaging apparatus defines a reconstruction volume comprising a plurality of voxels, wherein X-rays intersect each voxel of the reconstruction volume at a plurality of angles and wherein said plurality of angles are substantially evenly distributed over a range of 0 degrees to 360 degrees.

8. An X-ray imaging apparatus of claim 1 further comprising a plurality of sensors arranged in a second ring around the object for detecting X-rays emitted from the plurality of X-ray sources after passing through the object, wherein the sensors are offset from the X-ray sources along a predefined axis.

9. An X-ray imaging apparatus for obtaining a radiation image of an object having a length, comprising:
 a plurality of X-ray tubes, each X-ray tube comprising a predefined number of X-ray sources and each X-ray source emitting X-rays during a predefined emission period, wherein the X-ray sources are arranged in a circular pattern on a plane that is normal to a direction of travel of the object; and
 a controller configured to cause each of said X-ray sources to emit X-rays in accordance with a firing pattern, wherein said firing pattern causes said sources to fire in a sequence that is rotationally invariant.

10. The X-ray imaging apparatus of claim 9 wherein, during operation, the X-ray tubes are stationary.

11. The X-ray imaging apparatus of claim 10 wherein the object travels on a conveyor belt having a speed in a range of 250 mm/s to 500 mm/s.

12. The X-ray imaging apparatus of claim 9 wherein the firing pattern causes an even distribution of X-rays from the X-ray sources over a surface of a virtual cylinder, having a length, wherein the virtual cylinder is positioned around the object and the length of the virtual cylinder is equal to or greater than the length of the object.

13. The X-ray imaging apparatus of claim 12 wherein the length of the virtual cylinder is equal to the length of the object plus a distance, wherein said distance is within a range of 0 mm to 100 mm.

14. The X-ray imaging apparatus of claim 9 further comprising a plurality of detectors for generating projection data, wherein the controller modifies the firing pattern based upon said projection data.

15. The X-ray imaging apparatus of claim 9 further comprising a plurality of detectors for generating projection data, wherein the sources and detectors, taken in combination, exhibit multi-fold symmetry.

16. An X-ray imaging apparatus defining a reconstruction volume, comprising a plurality of voxels, for scanning an object, comprising:
 a plurality of X-ray tubes, each X-ray tube comprising a predefined number of X-ray sources and each X-ray source emitting X-rays during a predefined emission period, wherein, during operation, the X-ray sources are stationary and wherein the X-ray sources are positioned in a plane;
 a plurality of detectors, wherein the detectors are on at least one plane that is parallel to the plane of the sources and for which the detectors and the sources are not co-planar and wherein the detectors generate projection data; and
 a controller configured to cause each of said X-ray sources to emit X-rays in accordance with a firing pattern, wherein said firing pattern causes the X-ray sources to emit X-rays that intersect each voxel of the reconstruction volume at a plurality of angles and wherein said plurality of angles are substantially evenly distributed over a range of 0 degrees to 360 degrees and wherein the firing pattern causes a substantially even distribution of X-rays from the X-ray sources over a surface of a virtual cylinder, having a length, wherein the virtual cylinder is positioned around the object and the length of the virtual cylinder is equal to or greater than the length of the object.

17. The X-ray imaging apparatus of claim 16 wherein the length of the virtual cylinder is equal to the length of the object plus a distance, wherein said distance is within a range of 0 mm to 100 mm.

* * * * *